United States Patent [19]

Miller et al.

[11] Patent Number: 4,857,337

[45] Date of Patent: Aug. 15, 1989

[54] ENTERIC COATED ASPIRIN TABLETS

[75] Inventors: Ronald W. Miller, Langhorn, Pa.; Raymond W. Sutton, Medford, N.J.

[73] Assignee: American Home Products Corp. (Del), New York, N.Y.

[21] Appl. No.: 197,888

[22] Filed: May 24, 1988

[51] Int. Cl.$^4$ .............................................. A61K 9/36
[52] U.S. Cl. .................................... 424/480; 424/482
[58] Field of Search ................................ 424/480, 482

[56] References Cited

U.S. PATENT DOCUMENTS

| | | |
|---|---|---|
| 3,350,270 | 10/1967 | Gaunt ................................. 424/480 |
| 3,431,338 | 3/1969 | Munzel ............................... 424/480 |
| 4,302,440 | 11/1981 | John et al. ...................... 424/480 X |
| 4,556,552 | 12/1985 | Porter et al. ................... 424/480 X |
| 4,601,895 | 7/1986 | Streuff et al. ................... 424/480 X |
| 4,693,896 | 9/1987 | Wheatley et al. ................... 424/480 |
| 4,704,295 | 11/1987 | Porter et al. ................... 424/480 X |
| 4,775,536 | 10/1988 | Patell ............................. 424/480 X |

Primary Examiner—Thurman K. Page
Attorney, Agent, or Firm—John W. Routh

[57] ABSTRACT

Enteric coated aspirin tablets rendered shock-insensitive by the provision of a protective coat of hydroxyproply methylcellulose of at least about 1.5% by weight based on the weight of the tablet core.

3 Claims, No Drawings

ENTERIC COATED ASPIRIN TABLETS

FIELD OF THE INVENTION

This invention relates to enteric coated aspirin tablets or caplets protected against shock sensitivity. More particularly this invention relates to enteric coated shock-insensitive aspirin tablets protected against microfissures in the enteric coating by a protective coating of hydroxypropyl methylcellulose, the enteric coating and the protective coating each being applied from an aqueous solution or dispersion.

Two U.S. patent to Porter et al, i.e. U.S. Pat. Nos. 4,556,552 and 4,704,295, disclose non-toxic edible film coating dry powders and aqueous enteric coating suspensions for coating pharmaceutical tablets. The dry powders and aqueous suspensions include polyvinylacetate phthalate, a platicizer such as polyethylene glycol, an auxiliary film-forming polymer such as microcrystalline cellulose, fumed silica and optionally pigment materials. The patents teach that the enteric coating should comprise 5-10% of the weight of the tablet in order to get the enteric result and that the tablets may be pre-coated with a water soluble polymer solution to provide a smooth surface on an otherwise rough core.

U.S. Pat. No. 4,302,440 to John et al discloses a polymer film coated aspirin tablet in which the film coating polymer is hydroxypropyl methylcellulose and a plasticizer, such as triacetin, applied to the aspirin core from an aqueous solution. The film coat is applied in an amount of between 0.5 and 2.0 parts by weight per 100 parts by weight of the aspirin tablet.

SUMMARY OF THE INVENTION

According to this invention, enteric coated shock sensitive aspirin tablets/caplets are made shock insensitive by application to the enteric coated tablet/caplet of a protective coating from an aqueous solution of hydroxypropyl methylcellulose in an amount of about 1.5% to about 5% based on the weight of the aspirin tablet/caplet core. The aspirin tablet/caplet core may or may not be provided with a film undercoat of up to about 0.7%, preferably 0.2 to about 0.5% based on the weight of the aspirin tablet/caplet core of hydroxypropyl cellulose, hydroxypropyl methylcellulose or mixtures thereof. The enteric coat is applied from an aqueous suspension of polyvinylacetate phthalate in an amount of about 7% to about 12% based on the weight of the tablet core.

DETAILS OF THE INVENTION

Enteric coated aspirin tablets were prepared in a commercial size 67 inch diameter coating pan in accordance with the teachings of U.S. Pat. Nos. 4,556,552 and 4,704,295 using the material marketed by the assignee of the patents, Colorcon, Inc. of West Point, PA, under the trademark "Coateric White YPA-6-7089". The tablet cores contained 325 milligrams of aspirin and they were film coated with hyroxypropylmethyl cellulose. The enteric coating comprised 11% by weight based on the weight of the cores. As described in the patent, the enteric coated tablets, when carefully removed from the coating pan, passed the U.S.P. enteric test. It was found, however, that when the enteric coated tablets were removed from the pan as in commercial production, i.e. by discharging the contents of the pan into a stainless steel holding bin, the shock of the falling of the tablets from two to three feet and the impinging of the falling tablets upon the tablets already in the holding bin, created microfissures in the enteric coating which could not be seen under a microscope but which nevertheless caused the enteric coated tablets to fail the U.S.P. enteric test.

In order to protect these shock-sensitive enteric coated aspirin tablets from developing microfissures during further commercial processing of the tablets, a protective polymer coating was applied. The coating polymer was hydroxypropyl methylcellulose applied from an aqueous solution in an amount of about 1.5% to 5% based on the weight of the tablet core, preferably about 1.5% to about 3% by weight. It was found that a normal polishing coat of hydroxypropyl methylcellulose cellulose of up to about one percent based on the weight of the tablet core was not sufficient to render the enteric coated aspirin tablets shock-insensitive.

Typical enteric coated shock insensitive aspirin tablets of this invention and details of their preparation are described in the following examples.

EXAMPLE 1

The tablet core formulaton of this example contains the materials shown below in milligrams per tablet.

| Ingredients | Mg./Tablet |
| --- | --- |
| aspirin 20/40 mesh, USP | 325.00 |
| Starch 1500 | 18.75 |
| Microcrystalline Cellulose, NF | 79.00 |
| Sodium Lauryl Sulfate, NF | 0.25 |
| | Total 423 mg |

The tablet ingredients were blended and fed into a high speed commercial size tablet press to provide tablet cores each weighing approximately 423 milligrams.

Cores were charged to the commercial size Hi-Coater Unit having a 67 inch diameter coating pan in the amount of 325 kilograms or approximately 768,000 tablet cores.

The materials used in the coating operation are set forth below with respect to the specific coating steps.

The Undercoat

The undercoat material employed was a commercial product marketed by Colorcon, Inc. of West Point, Pa as "Opadry Clear YS-2-7013." This material is said to be hydroxypropyl methylcellulose with about 20% by weight polyethylene glycol as the plasticizer. The undercoat was applied from an aqueous solution containing 5% solids in an amount to provide an increase in the weight of the tablet of about 0.5% by weight based on the weight of the core. The undercoat solution charged to the Hi-Coater Unit feed tank amounted to 35 kilograms.

The parameters of operation for the coating unit during the undercoat application step were as follows:

| | Cycle Number | | |
| --- | --- | --- | --- |
| | 1 | 2 | 3 |
| Spray Time, minutes | 0–30 | 30–65 | 65–end |
| Temp. Set Point, °C. | 86 | 84 | 78 |
| Air Inlet Temp., °C. | 78–80 | 78–80 | 70–75 |
| Air Outlet Temp., °C. | 40–43 | 40–43 | 40–43 |
| Pan Speed, R.P.M. | 4 | 5 | 5 |
| Spray Rate, ml/min | 100 | 125 | 110 |
| Number of Guns | 4 | 4 | 4 |

Tablet weight (average of 100 tablets) was determined periodically until the average tablet weight was 423.7 milligrams. The undercoated tablets were dried in the rotating pan and the coating system including the spray guns, tanks, pumps and lines were cleaned.

The Enteric Coat

The enteric coating material employed was a commercial product marketed by Colorcon, Inc. of West Point, PA as "Coateric White YPA-6-7089." This material is said to contain polyvinylacetate phthalate, aluminium hydrate, polyethylene glycol as a plasticizer, stearic acid, titanium dioxide as a pigment and sodium alginate as an auxiliary film forming polymer and suspending agent. The proportions are generally as set forth in U.S. Pat. No. 4,556,552 herein incorporated by reference in its entirety. The "Coateric" dry powder is mixed with water to form an aqueous suspension or dispersion containing about 15% solids.

The aqueous "Coateric" suspension is admixed with concentrated ammonium hydroxide in an amount of about 40 milliliters ammonium hydroxide solution per 1000 grams of "Coateric" powder. The ammonium hydroxide serves as an anti-coalescing or stabilizing agent to prevent clogging problems with the spray equipment. The enteric coating dispersion charged to the Hi-Coater Unit feed tank amounted to approximately 311 kilograms.

The undercoated cores having an average tablet weight per 100 tablets of 423.7 milligrams remaining in the Hi-Coated Unit coating pan amounted to 326 kilograms. The enteric coating was applied from the aqueous suspension containing about 15% solids in an amount to provide about an 11.0% weight gain based on the weight of the core.

The parameters of operation for the coating unit during the enteric coating application step were as follows:

| Spray Time | 645 minutes |
|---|---|
| Temp. Set Point | 80° C. |
| Air Inlet Temp. | 70–75° C. |
| Air Outlet Temp. | 37°–40° C. |
| Pan Speed | 6.8 RPM |
| Spray Rate | 133–135 ml per min. per gun |
| Number of Guns | 4 |

Tablet weight (average of 100 tablets) was determined half-hourly until the average tablet weight reached 471.7 milligrams after 10 hours and 45 minutes when spraying was stopped. The enteric coated tablets were dried in the rotating pan and the coating system including the spray guns, tanks, pumps and lines were cleaned.

The Protective Coat

The protective coating material employed was a mixture of commercial products marketed by Dow Chemical Company, Midland, Mich., as "Methocel E-5 Premium" and "Methocel E-15 LV Premium", USP grades. These materials are grades of hydroxypropyl methylcellulose having a methoxyl content of 28–30% and a hydroproxypoxyl content of 7–12%, a number average viscosity of a two percent aqueous solution at 20° C. of 4000 and an average molecular weight of about 86,000.

The polymers are dissolved in 85,700 grams of water in the amounts of 5290 grams Methocel E-5 and 2640 grams Methocel E-15 together with Polyethylene Glycol 3350 NF in the amount of 1590 grams as a plasticizer to provide about 10% total weight by weight solids in aqueous solution. The protective coating solution charged to the Hi-Coater Unit feed tank amounted to 70.5 kilograms.

The enteric coated cores having an average tablet weight per 100 tablets of 471.7 milligrams remaining in the Hi-Coater Unit coating pan amounted to 310 kilograms. The protective coating was applied from the aqueous solution containing about 10% solids in an amount to provide an increase in the weight of the tablet of about 2.5% by weight based on the weight of the core.

The parameters of operation for the coating unit during the protective coating application step were as follows:

| Spray Time | 150 minutes |
|---|---|
| Temp. Set Point | 85–86° C. |
| Air Inlet Temp. | 74–75° C. |
| Air Outlet Temp. | 43–45° C. |
| Pan Speed | 6 RPM |
| Spray Rate | 120 ml per min. per gun |
| Number of Guns | 4 |

Tablet weight (average of 100 tablets) was determined every 5 or 10 minutes until the average tablet weight reached 481 milligrams after 150 minutes when spraying was stopped. After the coating process was completed, the tablets were dried at a pan speed of 2 RPM for four minutes with the air temperature at 80° C. and then for five minutes with the air heater cut off. The yield was aoubt 657,000 tablets having an average tablet weight per 100 tablets of 481 milligrams.

After the drying cycle, the tablets were scooped by hand into tared containers each lined with a polyethylene bag after which each bag was tied, sealed and labelled.

In order to protect the coated aspirin tablets against decomposition of the acetylsalicylic acid into acetic acid and salicyclic acid, it is advisable to incorporate into the tablet core a small amount of citric, alginic or glutamic acids, or mixtures thereof, as described in Blank and Miller U.S. Pat. No. 4,716,042.

EXAMPLE 2

The increase in the weight of the tablets with time during the protective coating application of Example 1 is shown in the following table as determined during the periodic withdrawal of tablets for tablet weight determination.

| Elapsed Time | Weight Mg/tablet | Percent HPMC |
|---|---|---|
| 0 | 470 | 0 |
| 30 minutes | 472.2 | 0.5% |
| 60 minutes | 474.2 | 1.0% |
| 90 minutes | 476.5 | 1.5% |
| 120 minutes | 480.2 | 2.0% |
| 150 minutes | 481.0 | 2.5% |

Several thousand tablets were withdrawn from the coating pan at each of these time periods in order to perform dissolution and shock insensitivity tests.

The dissolution tests were performed in accordance with Method B as set forth in the 5th Supplement of USP-XX1, pages 2465 and 2466, under the heading "(724) Drug Release" and the sub-heading "Delayed-release (Enteric-coated) Articles-General Drug Release Standards". The results of these tests for the acid stage and the buffer stage are shown in the following tables:

| Percent Dissolved Against Time - Six Tests | | | | | | |
|---|---|---|---|---|---|---|
| Elapsed Time Test Number (Acid Stage) 0% HPMC | | | | | | |
| | 1 | 2 | 3 | 4 | 5 | 6 |
| 120 minutes | 0 | 0 | 0 | 0 | 0 | 0 |

| Percent Dissolved Against Time - Six Tests | | | | | | |
|---|---|---|---|---|---|---|
| Elapsed Time Test Number (Buffer Stage) 0% HPMC | | | | | | |
| | 1 | 2 | 3 | 4 | 5 | 6 |
| 30 minutes | 7 | 7 | 9 | 7 | 22 | 7 |
| 60 minutes | 95 | 89 | 86 | 72 | 97 | 93 |
| 90 minutes | 106 | 101 | 110 | 92 | 98 | 101 |

The above test data show that the enteric coated aspirin tablets without the protective coating pass the dissolution tests in that the tablets are not dissolved in the acid test (simulating stomach conditions) but are substantially dissolved in 60 minutes in the buffer test (simulating intestine conditions). These tablets had been hand scooped from the coating pan and had not been discharged from the coating pan under commercial conditions where they would have been dropped into the lined containers for a distance of about two to three feet.

The enteric coated aspirin tablets with the protective coating in amounts of 0.5%; 1.0%; 1.5%; B 2%; and 2.5% were similarly tested in the buffer test in accordance with Method B as set forth in the 5th Supplement of USP-XX1. The data below show the average elapsed time from six tests for 60%, 75% and 80% of the aspirin content of the tablets to be dissolved for each tablet group.

| | Percent HPMC In Protective Coat | | | | | |
|---|---|---|---|---|---|---|
| % Dissolved | 0.0% | 0.5% | 1.0% | 1.5% | 2.0% | 2.5% |
| 60% | 48.5 | 44.3 | 49.3 | 47.8 | 42.8 | 44.7 |
| 75% | 53.0 | 48.7 | 53.5 | 52.8 | 47.2 | 48.2 |
| 80% | 55.5 | 50.8 | 56.2 | 54.8 | 50.0 | 50.0 |

The above test data show that the protective coating does not significantly affect the dissolution time of the enteric coated aspirin tablet in the buffer test (simulating intestine conditions).

EXAMPLE 3

A portion of the enteric coated tablets from the enteric coating step of Example 1 were further coated with the protective coating as in Example 1 to provide tablets with 3%, 4% and 5% of the hydroxypropyl methylcellulose protective coat of Example 1. These tablets were also subjected to the buffer test in accordance with Method B as set forth in the 5th Supplement of USP-XX1. The data below show that all enteric coated tablets passed the test. All tablets also passed the acid test.

| | Percent HPMC In Protective Coat | | |
|---|---|---|---|
| % Dissolved | 3% | 4% | 5% |
| 60% | 41.5 | 41.5 | 37.0 |
| 75% | 45.5 | 46.3 | 41.8 |
| 80% | 47.8 | 48.3 | 45.2 |

In order to determine the criticality of the amount of the protective coat applied in making the enteric coated aspirin tablets shock insensitive, a test was devised in which the enteric coated aspirin tablets from the enteric coating step of Example 1 were compared to the tablets of Example 1 having 2.5% hydroxypropyl methylcellulose protective coating.

In the test, the tablets were dropped into a stainless steel bucket from a height of approximately three feet, at least 500 tablets from each batch. The dropped tablets were then immersed in a 0.1N HCl bath and the number of swollen$^{(S)}$ and ruptured$^{(R)}$ tablets were counted periodically. The results are shown in the following table and establish the shock sensitivity of the tablets without the protective coating when dropped in that almost 25% ruptured and released their aspirin content within 10 minutes.

| Elapsed Time Minutes | 0.0% HPMC Not Dropped R&S/10,000 | 0.0% HPMC Dropped R&S/1,000 | 2.5% HPMC Dropped R&S/2,000 |
|---|---|---|---|
| 5 | 0 R | | 1R |
| 10 | | 220 R | 2R |
| 15 | 2R | | 3R |
| 30 | 2R | | 3R |
| 45 | 2R | | |
| 60 | 2R | | 3R 60S |
| 90 | 2R 2S | 296R | |
| 120 | 3R 2S | 299R | 3R 165S |
| 180 | 3R 4S | | 3R 232S |
| 240 | 3R 6S | 346R | 3R 290S |

The above test was repeated in order to determine the percent hydroxypropyl methylcellulose in the protective coating required to make the enteric coated tablets shock insensitive. The enteric coated tablets from Example 2 having from 0.5% to 2.0% hydroxypropyl methylcellulose in the protective coating were subjected to the same drop test and the results are presented below. There were 500 tablets in each group tested. None of the enteric coated tablets of this example which had not been dropped ruptured after 5 hours immersion and no tablets which had not been dropped were swollen until after 1 hour immersion.

| Elapsed Time, Minutes | 0.5% HPMC Dropped R&S/500 | 1.0% HPMC Dropped R&S/500 | 1.5% HPMC Dropped R&S/500 | 2.0% HPMC Dropped R&S/500 |
|---|---|---|---|---|
| 5 | 34 R | 8R | 0 | 0 |
| 10 | 39 R | 10R | 0 | 0 |
| 15 | 51 R | 10 R | 0 | 0 |
| 30 | 52 R 8S | 10 R 7S | 6S | 3S |
| 60 | 52 R 22S | 10 R 35S | 35S | 12S |
| 120 | 53 R 111S | 10 R 111S | 96S | 60S |
| 180 | 53 R 144S | 10 R 134S | 129S | 86S |
| 240 | 53 R 152S | 10 R 136S | 147S | 100S |
| 300 | 53 R 161S | 10 R 148S | 154S | 116S |

The above test data show that a hydroxypropyl methylcellulose content in the protective coating of about 1.5% is required to prevent rupturing or failure and premature release of aspirin from the enteric coated tablets. The Example 3 data show that a hydroxypropyl methycellulose protective coating of about 5% provides adequate enteric dissolution results. Hence a percentage of hydroxypropyl methylcellulose higher than 5% would not appear to serve any useful purpose.

Although Methocel E-5 and Methocel E-15 grades of hydroxypropyl methylcellulose were employed in Example 1, other grades of hydroxypropyl methylcellulose can be used such as U.S.P. Hydroxypropyl Methylcellulose 2910; U.S.P. Hydroxypropyl Methylcellulose 2208; and Hydroxypropyl Methylcellulose 2906. Polyethylene glycol is the preferred plasticiser and is used in an amount of about 12% to 25% by weight of the total coating solids.

The undercoat or film coat is also preferably hydroxypropylmethyl cellulose and the plasticiser is preferably polyethylene glycol in an amount of about 15% to 25% weight by weight of plasticiser based on the hydroxypropylmethyl cellulose as taught in the John et al U.S. Pat. No. 4,302,440.

We claim:

1. An enteric coated aspirin tablet/caplet comprising
   (i) a tablet core consisting essentially of about 300-500 milligrams of aspirin as the principal active ingredient admixed with pharmaceutically acceptable excipients,
   (ii) a film coat comprising up to about 0.5% based on the weight of the core of a cellulose polymer selected from the group consisting of hydroxypropyl methylcellulose, hydroxypropyl cellulose and mixtures thereof,
   (iii) an enteric coat consisting essentially of polyvinylacetate phthalate in an amount of about 7% to about 12% by weight based on the weight of the core,
   (iv) a protective coat consisting essentially of about 1.5% to about 5% by weight based on the weight of the core of hydroxypropyl methylcellulose, each of the film coat, the enteric coat and the protective coat having been applied from an aqueous solution or suspension of a film or enteric coating material.

2. The enteric coated aspirin tablet/caplet of claim 1 wherein the protective coat consists essentially of about 2.5% by weight based on the weight of the core.

3. The enteric coated aspirin tablet/caplet of claim 1 wherein the protective coat contains about 12% to 25% by weight polyethylene glycol as a plasticiser.

* * * * *